United States Patent [19]  
Takinishi et al.

[11] 4,175,338  
[45] Nov. 27, 1979

[54] ARTIFICIAL PALATE FOR USE IN DYNAMIC PALATOGRAPHICAL SPEECH RESEARCHES AND IMPROVEMENTS AND METHOD OF FABRICATING THE SAME

[75] Inventors: Kiyotoshi Takinishi; Junichi Hattori, both of Tokyo, Japan

[73] Assignee: Rion Co., Ltd., Tokyo, Japan

[21] Appl. No.: 837,039

[22] Filed: Sep. 27, 1977

[30] Foreign Application Priority Data

Sep. 29, 1976 [JP] Japan .................... 51-117009

[51] Int. Cl.$^2$ ............................................. G09B 19/04
[52] U.S. Cl. ..................................... 35/35 R; 35/17; 29/627
[58] Field of Search .................. 35/35 R, 17; 29/627; 128/2 S; 3/1.1

[56] References Cited

U.S. PATENT DOCUMENTS

| 3,509,624 | 5/1970 | Boucher ........................ 29/627 X |
| 4,112,596 | 9/1978 | Fletcher et al. ................... 35/35 R |

OTHER PUBLICATIONS

*Dynamic Palatometry*, reprinted from "Journal of Speech and Hearing Research" Dec. 1975, vol. 18, No. 4, pp. 812–819.

*Primary Examiner*—William H. Grieb
*Attorney, Agent, or Firm*—Burns, Doane, Swecker & Mathis

[57] ABSTRACT

Improved artificial palate for use in dynamic palatographical speech researches and improvements in the method of fabricating such artificial palate are provided. The artificial palate comprises a shell body mold-formed with an electrically insulative plastic material in conformity with individual user's palate. A flexible insulative circuit board includes a plurality of sensing electrodes provided in the board over the area thereof and lead wires printed on both surfaces of the board for connecting the respective electrodes to terminals arranged on both surfaces of the board adjacent an edge thereof. The circuit board is embedded in the shell body exposing the sensing electrodes on the inner surface of the body to be in contact with user's tongue during the use. Insulation coated wires connect the electrode terminals to the exterior and form means for mounting the artificial palate in user's mouth when embedded in the plastic material contiguous to the shell body. In the fabricating method, the circuit board is preliminarily prepared in different sizes, a proper size of the circuit board is selected to be joined to the mold-formed shell body, and the plastic material is applied over the board to embed it in the body but exposing the sensing electrodes on the tongue contacting surface.

5 Claims, 6 Drawing Figures

ARTIFICIAL PALATE FOR USE IN DYNAMIC PALATOGRAPHICAL SPEECH RESEARCHES AND IMPROVEMENTS AND METHOD OF FABRICATING THE SAME

This invention relates to artificial palates for use in dynamic palatographical speech researches and improvements and methods of making the same.

Dynamic palatography involves electrically detecting the contacting modes of a human tongue with the palate during speeches in the form of momentary patterns and continuously observing such patterns. Movements of the tongue during speech are basic factors of articulation and the dynamic palatography performs a great role in articulatory improvements of speech and hearing disorders by utilizing the observation of physiological movements of the tongue.

The artificial palate to be used in the dynamic palatography is to fit intimately with the palate of an individual who wears. The artificial palate comprises many fine sensing electrodes distributed in a main palate body made of such insulating material as a synthetic resin, and lead wires connected to these sensing electrodes. In the dynamic palatographic observation, the lead wires are led out of the individual's mouth and connected to a palatography device. A low pulse voltage is applied to the tongue from outside through such part of the individual's body as an earlobe or the like There are then detected patterns of the sensing electrodes to which an electric current is flowed through the tongue momentarily by physiological contacts between the tongue and the artificial palate or, in other words, between the tongue and the sensing electrodes during the speech. Such detection of patterns allows the continuous observations to be made of the momentary contact patterns of the tongue.

Conventionally, in fabricating the artificial palate, as shown in FIGS. 1 and 2, a plaster mold of the palate of an individual who will use the artificial palate is taken and an instantaneously polymerizable resin in a molten state is poured over this plaster mold on its outer surface to be brought into contact with the user's own palate to make a shell body 1 of a thickness of about 0.5 mm. At this time, a pair of wires 2 of a diameter of about 0.5 mm. to be wound on the outer peripheries of inner teeth of the user for holding the artificial palate in place are provided. The wires as embedded at one end in the body 1 and extended at the other end from both side ends of the body 1. Then, many holes are made in any desired distribution at proper intervals over the entire surface of the body. Sensing electrodes 3 each made of a gold chip of a diameter of about 1 mm. are fitted and fixed respectively in these holes. Then lead wires 4 are connected to the respective sensing electrodes 3 on the other inner surface of the body with which the user's tongue is to contact. The lead wires 4 are coated with insulation, bonded along the inner surface of the body 1 and collected at both side ends of the body in the form of lead wire bundles 5. The lead wire bundles 5 are led out of the user's mouth along the outsides of the upper teeth and the ends of lips. It is in consideration of undesirable troubles caused by ionization that gold is selected for the material of the sensing electrode.

The artificial palate made by such conventional technique as described above is finished by filing after the sensing electrodes are placed, so that the inner surface of the body 1 (which the tongue is to contact) as well as the exposed surface of the respective sensing electrodes 3 will be flush with each other. Thus many steps and a skill have been required. Further, it has been difficult to treat many lead wires and there have been problems involving mis-wiring and unfavorable conduction are likely to occur. Because the wires for holding the palate body are wound on the inner teeth, the fitting feeling may be bad and the lead wire bundles may be bitten into so as to impair or even damage them during the speaking.

The present invention has been suggested to remove such defects as above. According to the present invention, the problems have been successfully solved by using a printed circuit on a flexible base plate for the assembly of the sensing electrodes and employing lead-out wiring for the electrodes.

A primary object of the present invention is, therefore, to provide an artificial palate wherein improved means for holding the palate body and means for leading out the lead wire bundles are employed, whereby any unpleasant feeling during use, as well as the risk of damaging the lead wires are effectively reduced.

Another object of the present invention is to provide an artificial palate which can be fabricated easily and economically.

A further object of the present invention is to provide an improved method of fabricating artificial palates which is adapted to a mass-production.

Another object of the present invention is to provide an improved method of fabricating artificial palates which involving no risks of mis-wiring and unfavorable conduction during the fabrication.

The present invention shall now be detailed in the followings with reference to certain preferred embodiments shown in accompanying drawings, in which.

Figure 1:
FIG. 1 is a plan view of a frame body of a conventional artificial palate.
Figure 2:
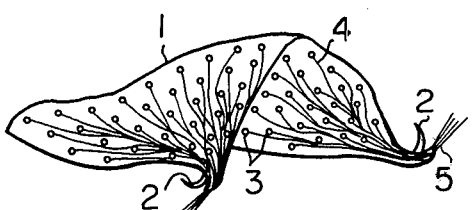
FIG. 2 is a perspective view of a completed artificial palate using the frame body of FIG. 1.
Figure 3:
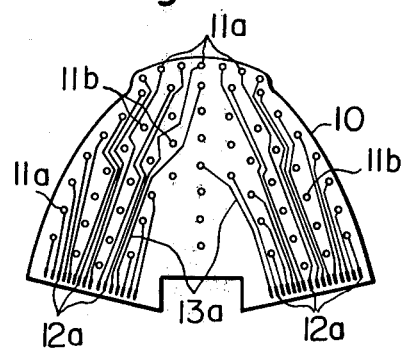
FIG. 3 is a plan view of a first surface of a both-surface printed board used in an embodiment of the artificial palate according to the present invention.
Figure 4:
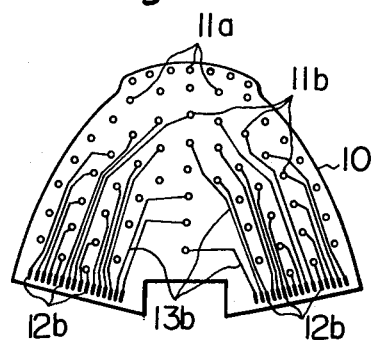
FIG. 4 is a plan view of a second surface of the printed board in FIG. 3.
Figure 5:
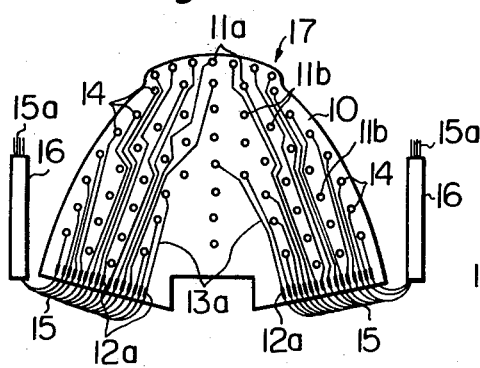
FIG. 5 is a plan view of the first surface of the printed board of FIG. 3 but with lead wires assembled.

Referring to a preferred embodiment of the present invention with reference to FIGS. 3 to 6, a printed wiring circuit made of, for example, a copper foil of a thickness of 18 to 35 microns is provided on each of both surfaces of a flexible and electrically insulative base board 10 made of, for example, a polyester or polyimide film of a thickness of 25 microns. This base board 10 is prepared in a flat state but having an outline and area adapted to any user's palate. A plurality of through holes 11a and 11b are made in the positions in which sensing electrodes are to be arranged. These holes are usually distributed symmetrically over the entire area of the board including its central and both side regions with a maximum total number of about 64 holes but the distribution pattern and total number of the holes are to be properly selected as desired. Electrically conductive wires 13a and 13b to be led out of these holes towards a peripheral part of the board 10 are provided by means of a proper printing technique. Preferably the printing is performed on the respective surface of the board 10 as divided substantially into halves with respect to substantially each half of the holes 11a and 11b as indentified in FIGS. 3 and 4 and also, on each of the surfaces, as divided into right and left groups with respect to further each one half of the respective halves of the holes 11a and 11b as seen in FIG. 3 or 4. Such two groups of the wires 13a or 13b on each surface of the board 10 are respectively led towards two straight edges of the board, where they are connected to respective terminals 12a or 12b also printed in arrays adjacent the edges on each surface of the board, as shown in FIG. 3 or 4. For the printing technique of the wires 13a and 13b as well as the terminals 12a and 12b, it is preferable to employ, for example, an etching and throughhole plating technique. On the base board 10 on which the wiring and their terminals are thus provided, as shown in FIG. 5, sensing electrodes 14 are then fitted in the respective holes 11a and 11b and insulation-coated lead wires 15 are fused and connected at their end parts to the terminals 12a and 12b to complete a printed board 17 for the artificial palate. Reference numeral 16 indicates a proper sleeve which covers each of a pair of bundles 15a of the lead wires 15.

It will be appreciated that several kinds of sizes of the printed board 17 are prepared so that they can be selectively used for all individuals, whereby a mass-production of the artificial palate is made possible.

While in the above described embodiment the wirings from the sensing electrodes to the terminals are provided as divided into halves on the respective surfaces of the printed board, it will be also appreciated that the whole wirings can be provided only on one surface of the board.

Now, in order to prepare a main body of the artificial palate, a plaster mold of the palate of an individual user is taken very precisely over the entire area of the user's palate to the extent of teeth and tooth stems. Then, an instantaneously polymerizable resin in molten state is poured into this plaster mold to form a thin shell-shaped main body of a size covering the palate area surrounded by the teeth. In this case, such substance as an acrylate or silicone is preferably used for the instantaneously polymerizable resin.

Then the before described printed board 17 is intimately joined on its one surface to the inner surface with which the tongue is to contact of this main body by such proper means as a gluing or the like. Further, to the other surface of the printed board thus joined, the same kind of the instantaneously polymerizable resin is applied to cover the surface integrally therewith. In this step, as the base board 10 of the printed board 17 is a flexible film, it will easily and intimately conform to the inner surface of the main body which is concavely curved.

Figure 6:
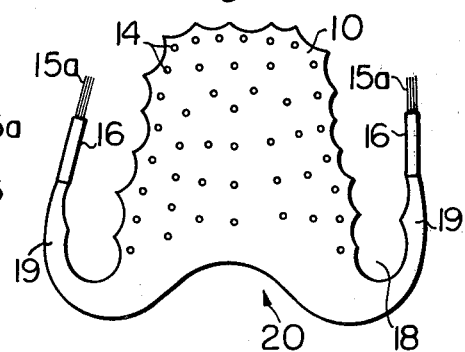
FIG. 6 is a plan view of the artificial palate as completed with the printed board shown in FIGS. 3 to 5 according to the present invention.

Further, extended parts of the lead wires 15 and lead wire bundles 15a in the sleeves 16 are also coated with the same instantaneously polymerizable resin to be contiguous to and integral with the main body while being bent to be curved at their tips in outward directions of the mouth to form spaces 18 fitting both side inner teeth for holding them with arms 19 in which the lead wires are embedded, as shown in FIG. 6.

Finally, the thus joined assembly of the board 17 and main body is taken out of the plaster mold and is finished with a file to remove any fins and to smooth the surface on which the tongue is to contact the sensing electrodes so that an artificial palate 20 will be completed.

As described above, according to the present invention, the printed circuit board on which the sensing electrodes are arranged and their lead-out wirings are embedded in the form of a sandwich within the main body, so that the artificial palate can be fabricated easily and reliably without causing any risks of mis-wirings during the fabrication and of wire damages during the use.

Further, as the holding arms 19 for mounting the device to the user's palate are provided by utilizing the parts including the lead wire bundles to be led out of the mouth, unfavorable mounting feeling can be reduced and the problem of the lead wires being broken by biting can be eliminated.

What is claimed is:

1. An artificial palate for use in dynamic palatographical speech research and which is of the type comprising a structure to be intimately fitted to a particular user's palate, said structure including a plurality of sensing electrodes supported by said structure so as to be contacted by a user's tongue during use, lead wires each connected at one end to a respective electrode, the other ends of said wires extending from at least an end portion of the structure, and means on the structure for mounting the structure within the user's mouth, the improvement wherein said structure comprises:
    a shell body formed of electrically insulative material in the shape of a particular user's palate, and
    a base board formed separately of said shell body of flexible electrically insulative material, with said lead wires formed on said base board in the form of a printed circuit applied with said base board being substantially flat,
    said base board being secured to a lower surface of said shell body such that said lead wires are sandwiched therebetween, and said base board being held in the shape of the user's palate solely by the connection between said base board and said shell.

2. An artificial palate according to claim 1, wherein said means for mounting said structure within the user's mouth comprises a pair of arms extending from opposite sides of said structure, said arms each comprising: the portions of a plurality of said lead wires which extend from said structure, and a film of electrically insulative material encasing said wire portions.

3. An artificial palate according to claim 1, wherein said wire portions of each arm are disposed within a sleeve, said wire portions and said sleeve being embedded within a film of electrically insulative material.

4. An artificial palate according to claim 1, wherein substantially one-half of said lead wires extend from their respective electrodes along an upper surface of said base board and the remaining lead wires extend from their respective electrodes along a lower surface of said base board.

5. An artificial palate for use in dynamic palatographical speech research and which is of the type comprising a structure to be intimately fitted to a particular user's palate, said structure including a plurality of sensing electrodes supported by said structure so as to be contacted by a user's tongue during use, lead wires each connected at one end to a respective electrode, the other ends of said wires extending from at least an end portion of the structure, and means on the structure for mounting the structure within the user's mouth, the improvement wherein said means for mounting the structure within the user's mouth comprises a pair of arms extending from opposite sides of said structure, said arms each comprising: the portions of a plurality of said lead wires extending from said structure, a sleeve surrounding said wire portions, and a film of electrically insulative material encasing said sleeve and said wire portions.

* * * * *